United States Patent [19]
Koehler et al.

[11] Patent Number: 5,917,097
[45] Date of Patent: Jun. 29, 1999

[54] UNSATURATED FATTY COMPOUNDS WITH IMPROVED LOW-TEMPERATURE BEHAVIOR

[75] Inventors: Michael Koehler, Mettmann; Alfred Westfechtel, Hilden; Guenter Demmering, Solingen; Horst-Dieter Komp, Langenfeld; Christiane Boehr, Leverkusen; Achim Ansmann, Erkrath; Udo Steinberner, Hilden, all of Germany

[73] Assignee: Henkel Kommanditgesellschaft auf Aktien, Duesseldorf, Germany

[21] Appl. No.: 08/776,036

[22] PCT Filed: Jul. 7, 1995

[86] PCT No.: PCT/EP95/02646

§ 371 Date: Jun. 10, 1997

§ 102(e) Date: Jun. 10, 1997

[87] PCT Pub. No.: WO96/02619

PCT Pub. Date: Feb. 1, 1996

[30] Foreign Application Priority Data

Jul. 16, 1994 [DE] Germany .............. 44 25 180

[51] Int. Cl.$^6$ .................................... C07C 27/04
[52] U.S. Cl. .................. 568/884; 568/840; 568/876
[58] Field of Search ............... 568/884, 840, 568/876

[56] References Cited

U.S. PATENT DOCUMENTS 3,729,520  4/1973  Rutzen et al. .................... 260/638
4,338,221  7/1982  Qualeatti .......................... 252/455
5,276,204  1/1994  Schmid et al. .................... 568/616
5,399,792  3/1995  Demmering et al. .............. 568/864

FOREIGN PATENT DOCUMENTS 0370273   5/1990   European Pat. Off. .
1228603  11/1966   Germany .
4129622   3/1993   Germany .

OTHER PUBLICATIONS

Seifen–Ole–Fette–Wachse, vol. 109 (1983) pp. 225–230.
Ullmanns Encyklopaedie der technischen Chemie, Verlag Chemie, Weinheim, 4th ed., vol. 11, pp. 436, et seq.
Fat Sci. Technol., vol. 89, 1987, p. 297.
Fat Sci. Technol, vol. 89, 1987, p. 237.

*Primary Examiner*—Samuel Barts
*Assistant Examiner*—Deborah D. Carr
*Attorney, Agent, or Firm*—Ernest G. Szoke; Wayne C. Jaeschke; Real J. Grandmaison

[57] ABSTRACT

A process for producing unsaturated fatty compounds having improved low-temperature properties by
  a) splitting lauric oils into fatty acids and glycerol,
  b) subjecting the fatty acids to fractional crystallization to obtain a fraction of unsaturated fatty acids, and
  c) hydrogenating the unsaturated fatty acids, optionally after converting the unsaturated fatty acids into their lower alkyl esters, to form unsaturated fatty alcohols having an iodine value of from about 85 to about 100.

18 Claims, No Drawings

UNSATURATED FATTY COMPOUNDS WITH IMPROVED LOW-TEMPERATURE BEHAVIOR

This application is a 371 of PCT/EP95/02646 filed Jul. 7, 1995.

FIELD OF THE INVENTION

This invention relates to unsaturated fatty compounds with improved low-temperature behavior which are obtained by splitting selected vegetable oils into fatty acids and glycerol, subjecting the resulting split fatty acids to fractional crystallization and hydrogenating the accumulating fraction of substantially unsaturated fatty acids, optionally after conversion into the methyl esters, with the double bonds intact to form the corresponding fatty alcohols. The invention also extends to derivatives of the unsaturated fatty alcohols, to processes for their production and to their use for the production of surface-active formulations. Finally, the invention relates to the use of selected vegetable oils for the production of unsaturated fatty alcohols.

DISCUSSION OF RELATED ART

Fatty compounds, more particularly unsaturated fatty alcohols, are important intermediates for a large number of products of the chemical industry, for example for the production of surfactants and cosmetic products. An overview of this subject was published, for example, by U. Ploog et al. in *Seifen-Öle-Fette-Wachse* 109, 225 (1983).

Unsaturated fatty alcohols cannot be produced on the basis of petrochemical raw materials and processes. Instead, they are produced from more or less unsaturated fatty acids or methyl esters thereof based on renewable raw materials which are hydrogenated with the double bonds intact, for example in the presence of chromium- and/or zinc-containing mixed oxide catalysts [cf. *Ullmann's Enzyklopaedie der technischen Chemie*, Verlag Chemie, Weinheim, 4th Edition, Vol. 11, pages 436 et seq.].

Basically, unsaturated fatty alcohols can be produced in three ways:

1. Fats and oils are subjected to pressure hydrolysis with water. After removal of the water-containing glycerol, split fatty acids representing mixtures of saturated and unsaturated fatty acids are obtained. Since the co-hydrogenation of these acids is unable to influence the ratio of saturated and unsaturated components, it is only possible in this way to obtain fatty alcohols with a low iodine value below 85 which are less preferred.
2. Saturated and unsaturated $C_{16/18}$ fatty acids cannot be separated by distillation. In contrast to (1), however, the split fatty acids can be converted by so-called rolling-up into a predominantly saturated fatty acid cut and a predominantly unsaturated fatty acid cut. Hydrogenation of the unsaturated fatty acid cut gives technical oleyl alcohols with an iodine value in the range from about 85 to 100.
3. In addition, highly unsaturated vegetable oils can be subjected to transesterification in which methyl esters with a comparatively low percentage content of saturated homologs are obtained. In this case, rolling-up is neither possible nor necessary because the hydrogenation directly yields highly unsaturated fatty alcohols (I.V.>100).

The three processes mentioned have long been commercially used for the production of unsaturated fatty alcohols. It is logical to use starting materials already having a high iodine value for the production of unsaturated fatty alcohols.

Examples of suitable starting products for process 1 are fats and oils with an iodine value of 40 to 70, such as for example beef tallow, lard, palm oil or palm stearin. Suitable starting materials for the production of highly unsaturated fatty alcohols by process 3 are, for example, rapeseed oil, olive oil, sunflower oil, linseed oil or peanut oil.

Starting materials such as coconut oil or palm kernel oil, for example, have not hitherto been considered for the production of unsaturated fatty alcohols with iodine values in the range from 90 to 100 because they contain too small a percentage of unsaturated species.

Unfortunately, the unsaturated commercial fatty alcohols obtainable by the processes described above have various disadvantages. Products with an iodine value below 80 are wax-like. Apart from their unfavorable solidification point, they do of course only have some of the advantages associated with the unsaturated structure. Highly unsaturated fatty alcohols (iodine value>100) contain a significant percentage of polyunsaturated homologs and, for this reason, are not stable to autoxidation. Although the products are liquid, they are difficult to incorporate in creamy or paste-like formulations. From the performance point of view, therefore, unsaturated fatty alcohols with iodine values in the range from 85 to 100 are the most suitable. However, they are often unsatisfactory both in regard to their color and in regard to their odor quality and also have an unfavorably high solidification point for many applications.

Accordingly, the problem addressed by the present invention was to provide unsaturated fatty alcohols with an iodine value in the range from 85 to 100 based on vegetable raw materials—and corresponding derivatives—which would be distinguished in particular by improved low-temperature behavior and color and odor quality.

DESCRIPTION OF THE INVENTION

The present invention relates to unsaturated fatty compounds with improved low-temperature behavior obtainable by (a) splitting lauric oils into fatty acids and glycerol,
(b) subjecting the resulting split fatty acids to fractional crystallization and
(c) hydrogenating the fraction of predominantly unsaturated fatty acids, optionally after conversion into the lower alkyl esters, to form the corresponding unsaturated fatty alcohols with iodine values in the range from 85 to 100 and preferably in the range from 90 to 95.

It has surprisingly been found that, by using selected vegetable oils with a low iodine value range and by purifying the unsaturated fatty acids produced as intermediate stages on this basis in the hydrogenation step, it is possible for the first time to obtain unsaturated vegetable fatty alcohols which not only have extremely good color and odor properties, they are also distinguished as required by particularly advantageous low-temperature behavior. The use of the raw materials mentioned with their low iodine values in a process known per se, which for economic reasons has hitherto only been known for its application to raw materials with distinctly higher iodine values, appears to be new and inventive in view of the surprising effects observed.

Other advantageous embodiments of the invention are derivatives which also show favorable low-temperature behavior and improved color and odor properties and which are obtained by subjecting the unsaturated fatty alcohols mentioned at the beginning in known manner to alkoxylation;

alkoxylation, sulfation and neutralization;

sulfation and neutralization; or esterification with aliphatic carboxylic acids containing 1 to 22 carbon atoms and 0 and/or 1 to 3 double bonds.

Production process

The present invention also relates to a process for the production of unsaturated fatty compounds with improved low-temperature behavior, in which (a) lauric oils are split into fatty acids and glycerol, (b) the resulting split fatty acids are subjected to fractional crystallization and (c) the fraction of predominantly unsaturated fatty acids is hydrogenated, optionally after conversion into the lower alkyl esters, to form the corresponding unsaturated fatty alcohols with iodine values in the range from 85 to 100 and preferably in the range from 90 to 95.

Lauric oils

Lauric oils in the context of the invention are understood to be palm kernel oil, coconut oil and babassu oil and mixtures thereof in which the C chain distribution is centered on the $C_{12}$ to $C_{14}$ range. Typical compositions are shown in Table 1.

TABLE 1

Typical Composition of Palm Kernel Oil and Coconut Oil

| Fatty Acid Component | Palm Kernel Oil % By Weight | Coconut Oil % By Weight |
| --- | --- | --- |
| Caproic acid | 0–1 | 0–1 |
| Caprylic acid | 3–10 | 6–9 |
| Capric acid | 3–14 | 6–10 |
| Lauric acid | 37–52 | 44–51 |
| Myristic acid | 7–17 | 13–18 |
| Palmitic acid | 2–9 | 8–10 |
| Stearic acid | 1–3 | 1–3 |
| Oleic acid | 11–23 | 6–3 |
| Linoleic acid | 1–3 | 0–3 |
| Saponification value | 245–255 | 250–264 |
| Iodine value | 14–23 | 8–11 |
| Melting point (° C.) | 26—26 | 23–26 |

In the context of the invention, other fats and oils or mixtures thereof which also have iodine values of 5 to 25, a content of $C_{12-14}$ fatty acids of 30 to 55% by weight and a total linoleic (linolenic) acid content of <5% by weight, are regarded as direct equivalents which are encompassed by the present teaching.

It is preferred to use palm kernel oil from which a technical oleyl alcohol with an iodine value of 94, a solidification point of 7° C., a color of 10 Hazen and a composition of 5% by weight $C_{16}$ and 95% by weight $C_{18}$ can be produced by the process according to the invention.

Splitting

In the context of the invention, splitting is understood to be the saponification or hydrolysis of glycerol fatty acid (partial) esters into glycerol and fatty acids. The process goes back to E. Twitchell who, in 1898, developed a normal-pressure process for the splitting of triglycerides in which the hydrolysis was carried out in the presence of sulfuric acid and a mixture of naphthalene and oleic acid (Twitchell reagent). Since the development of suitable stainless steels in the thirties, the pressure hydrolysis of fats known since 1854 has also been carried out industrially with steam [cf. *Fat Sci. Technol.,* 89, 297 (1987)]. The latter process—besides the EMERSOL process—is preferred for the purposes of the invention.

Fractional crystallization and rolling-up

The separation of saturated and unsaturated $C_{16/18}$ fatty acids is carried out as fractional crystallization. It is preferably based on so-called rolling-up. Rolling-up is understood to be the separation of saturated and unsaturated fatty acids generally containing 12 to 18 and preferably 16 to 18 carbon atoms which are impossible or very difficult to separate by distillation on account of their very similar boiling points. A review of this subject was published by K. Schmid in *Fat Sci. Technol.,* 89, 237 (1987).

The process of rolling-up was developed at the beginning of the sixties for the separation of tallow fatty acid into a $C_{16/18}$ palmitic/stearic acid cut ("stearin") and an oleic acid fraction ("olein"), but is also applicable to split fatty acids with a broader C chain distribution. In the case of tallow fatty acid, the process is carried out by initially cooling the technical fatty acid mixture to low temperatures of around 5° C., the palmitic/stearic acid undergoing crystallization in the liquid oleic acid to form a dispersion. Although physical separation could be carried out here, it has been found that, in the case of filtration for example, excessively large amounts of oleic acid adhere to the palmitic/stearic acid crystals. In order to "wash off" the oleic acid from the crystals, an aqueous wetting agent solution, for example an aqueous alkyl sulfate is added to the dispersion. Subsequent centrifugation of this emulsion/dispersion results in breaking of the emulsion into an oleic acid phase and a water/saturated fatty acid dispersion which can be separated in a separator. The palmitic/stearic acid-water dispersion is then heated to around 50 to 80° C. and the molten palmitic/stearic acid is separated from the aqueous wetting agent solution which is returned to the process.

Hydrogenation

The reduction of esters with metallic sodium in the presence of an alcohol was discovered by Bouveault and Blanc in 1903. Nowadays, however, the production of fatty alcohols on an industrial scale is carried out almost exclusively by high-pressure hydrogenation of distilled or fractionated methyl ester or fatty acid cuts in one or more fixed-bed or shaft reactors arranged in tandem at temperatures of 200 to 250° C. and under a hydrogen pressure of 200 to 300 bar. To this end, the fatty acid or methyl ester is continuously forced into the installation against the hydrogen pressure, heated to the reaction temperature and introduced at the head of the reactor. Adkins catalyst beds based on Cu/Cr/Zn and/or Cu/Cr/Cd mixed oxides are normally used for the production of unsaturated fatty alcohols. In this case, the carboxyl(ate) group is selectively hydrogenated with the double bonds present in the fatty residue intact.

In addition to the fixed-bed procedure, the hydrogenation may also be carried out in the trickle phase. In this variant, too, fatty acid or ester and hydrogen flow through the reactor from above at a temperature of 200 to 300° C. and under a pressure of 250 to 300 bar. In this case, however, the quantities of recycle gas and the molar excess of hydrogen are considerably smaller which is reflected in smaller plant dimensions. Silica gel supported catalysts containing 20 to 40% by weight of the copper chromites mentioned at the beginning are used as catalysts. Although these catalysts have high mechanical stability, they are more susceptible to poisoning than solid catalysts on account of their low content of active substance and, accordingly, have shorter lives.

The resulting fatty alcohols are then preferably purified by distillation in known manner with removal of first runnings (around 5% by weight).

If desired, purification may be followed by a second fractional crystallization ("winterizing").

Mixtures

In another advantageous embodiment of the invention, the new unsaturated fatty alcohols based on palm kernel oil and/or coconut oil may be mixed with conventional saturated and/or unsaturated fatty alcohols containing 6 to 22 and preferably 16 to 18 carbon atoms. The advantage is that the mixtures also show improved performance properties.

For example, a mixture of 60 to 65% by weight of a technical oleyl alcohol according to the invention based on palm kernel oil and 35 to 40% by weight of a conventional oleyl alcohol (HD Ocenol® 60/65, Henkel KGaA) has a solidification point below 20° C. By contrast, the solidification point of an oleyl alcohol of comparable composition (HD Ocenol® 70/75, Henkel KGAA) based on beef tallow is 22° C.

Derivatization

As mentioned at the beginning, the present invention also includes the observation that the excellent properties of the unsaturated fatty alcohols initially produced remain intact even after derivatization. This includes:

Alkoxylation. Alkoxylates of the unsaturated fatty alcohols are obtained in known manner by addition of ethylene and/or propylene oxide in the presence of basic catalysts, for example sodium methylate or calcined hydrotalcite, and may have both a conventional homolog distribution and a narrow homolog distribution. The alkoxylates are suitable, for example, as raw materials for detergents, as emulsifiers in the textiles field, in drilling and cutting oils and in cosmetic formulations.

Alkoxylation/sulfation. Ether sulfates of the unsaturated fatty alcohols are obtained in known manner by alkoxylation, subsequent sulfation with gaseous sulfur trioxide or chlorosulfonic acid and, finally, neutralization with bases. The products are suitable as raw materials for detergents.

Sulfation. Fatty alcohol sulfates based on the unsaturated alcohols are obtained in known manner by sulfation with gaseous sulfur trioxide or chlorosulfonic acid and subsequent neutralization with bases. The products are also suitable as detergents for raw materials and as textile auxiliaries.

Esterification. Esters of the unsaturated fatty alcohols are obtained in known manner by catalytic reaction with aliphatic carboxylic acids containing 1 to 22, preferably 6 to 22 and more preferably 12 to 18 carbon atoms and 0 and/or 1 to 3 double bonds. Typical examples are reactions of a technical oleyl alcohol according to the invention (iodine value 95) with acetic acid, $C_{6-10}$ head-fractionated fatty acid, lauric acid, palmitic acid, stearic acid, oleic acid, $C_{12/14}$ cocofatty acid, $C_{12/18}$ cocofatty acid or $C_{16/18}$ tallow fatty acid. The esterification is preferably carried out with oleic acid to form an oleyl oleate. The products are suitable for example, as oils for the production of cosmetic formulations.

Other derivatizations which may also be considered include amidation, phosphatization, the formation of adducts with maleic anhydride and epoxidation, preferably after conversion of the oleyl alcohols into the methyl esters.

Commercial Applications

The unsaturated fatty compounds according to the invention are distinguished from known products by an improved odor, an improved color and, in particular, by more advantageous low-temperature behavior.

The present invention also relates to their use for the production of surface-active formulations such as, for example, superfatting agents or solvents for active substances, cremes, emollients and lotions, lubricants for the machining of metals and antifoam agents in dispersion paints, in which they may be present in quantities of 1 to 75% by weight and preferably 5 to 50% by weight, based on the particular product.

Finally, the present invention also relates to the use of lauric oils for the production of unsaturated fatty alcohols with iodine values of 85 to 100 and preferably 90 to 95 by splitting, fractional crystallization and hydrogenation.

EXAMPLES

General Production Procedures

Method 1. The starting materials were subjected to pressure hydrolysis and the glycerol/water mixture was removed. After conversion into the methyl ester, the resulting split fatty acid mixture was hydrogenated without further purification with the double bonds intact. The product was then purified by distillation.

Method 2. The starting materials were subjected to pressure hydrolysis and the glycerol/water mixture was removed. The resulting split fatty acid mixture was separated by rolling-up into a stearin fraction and an olein fraction. The olein, which contained around 80% by weight of oleic acid, was esterified with methanol and then hydrogenated with the double bonds intact. The product was then purified by distillation.

Method 3. The starting materials were transesterified with methanol and freed from glycerol and unreacted alcohol. The resulting methyl ester mixture was hydrogenated without further purification with the double bonds intact. The product was then purified by distillation.

The composition of the raw materials used is shown in Table 2 (percentages as % by weight). Table 3 shows the performance data of the resulting unsaturated fatty alcohols.

TABLE 2

Raw Materials Used

| Fatty Acid Component | PK % | CC % | BT % | PM % | PS % | OL % |
|---|---|---|---|---|---|---|
| Caproic acid | 1 | 1 | 0 | 0 | 0 | 0 |
| Caprylic acid | 4 | 8 | 0 | 0 | 0 | 0 |
| Capric acid | 5 | 7 | 0 | 0 | 0 | 0 |
| Lauric acid | 50 | 48 | 0 | 0 | 0 | 0 |
| Myristic acid | 15 | 17 | 3 | 2 | 4 | 10 |
| Palmitic acid | 7 | 9 | 27 | 42 | 72 | 3 |
| Stearic acid | 2 | 2 | 22 | 5 | 10 | 0 |
| Oleic acid | 15 | 7 | 43 | 41 | 11 | 80 |
| Linoleic acid | 1 | 1 | 5 | 10 | 3 | 7 |
| Iodine value | 19 | 9 | 44 | 50 | 15 | 82 |

Legend:
PK = Palm kernel oil
PM = Palm oil
CC = Coconut oil
PS = Palm stearin
BT = Beef tallow
OL = Olive oil

TABLE 3

Characteristic Data of the Products

| Ex. | Raw Material | I.V. | Method | SP °C. | Color Hazen | Odor |
|---|---|---|---|---|---|---|
| 1 | Palm kernel oil | 94 | 2 | 7.0 | 10 | +++ |
| 2 | Coconut oil | 91 | 2 | 8.5 | 15 | ++ |
| C1 | Palm kernel oil | 35 | 1 | 30.5 | 20 | + |
| C2 | Coconut oil | 35 | 1 | 32.0 | 25 | + |
| C3 | Beef tallow | 94 | 2 | 14.5 | 85 | − |
| C4 | Palm oil | 94 | 2 | 15.5 | 90 | − |
| C5 | Palm stearin | 94 | 2 | 17.0 | 90 | − |
| C6 | Olive oil | 112 | 2 | 7.0 | 25 | + |
| C7 | Olive oil | 108 | 3 | 7.0 | 120 | + |

Legend:
I.V. = Iodine value
SP = Solidification point
Odor = +++ = Odorless
++ = Odor hardly noticeable
+ = Odor noticeable
− = Odor distinctly noticeable Example 3

The unsaturated oleyl alcohol of Example 1 was esterified with palm kernel oil fatty acid (Edenor® PK 1805, Henkel KGaA). The resulting ester had the following characteristic data:

| | |
|---|---|
| Hydroxyl value | 209 |
| Iodine value | 94 |
| Saponification value | 0.3 |
| Solidification point | 7.2 |
| Color value (APHA) | 10 |

What is claimed is:

1. Unsaturated fatty alcohols having an iodine value of from about 85 to about 100 and improved low-temperature properties prepared by;
   a) splitting lauric oils having an iodine value of 5 to 25 into fatty acids and glycerol,
   b) subjecting said fatty acids to fractional crystallization to obtain a fraction of unsaturated fatty acids, and
   c) hydrogenating said unsaturated fatty acids, optionally after converting said unsaturated fatty acids into their lower alkyl esters.

2. Unsaturated fatty alcohols as in claim 1 wherein said lauric oils are selected from palm kernel oil and coconut oil.

3. Unsaturated fatty alcohols as in claim 1 wherein said lauric oils are subjected to pressure hydrolysis with water.

4. Unsaturated fatty alcohols as in claim 1 wherein said fractional crystallization step is carried out by rolling-up.

5. Unsaturated fatty alcohols as in claim 1 wherein said unsaturated fatty alcohols are alkoxylated.

6. Unsaturated fatty alcohols as in claim 1 wherein said unsaturated fatty alcohols are subsequently alkoxylated, sulfated and neutralized.

7. Unsaturated fatty alcohols as in claim 1 wherein said unsaturated fatty alcohols are subsequently sulfated and neutralized.

8. Unsaturated fatty alcohols as in claim 1 wherein said unsaturated fatty alcohols are subsequently esterified with aliphatic carboxylic acids containing 1 to 22 carbon atoms and 0 or 1 to 3 double bonds.

9. Unsaturated fatty alcohols as in claim 1 wherein said unsaturated fatty alcohols are mixed with other saturated or unsaturated fatty alcohols containing 6 to 22 carbon atoms.

10. The process of producing unsaturated fatty compounds having improved low-temperature properties comprising:
   a) splitting lauric oils having an iodine value of 5 to 25 into fatty acids and glycerol,
   b) subjecting said fatty acids to fractional crystallization to obtain a fraction of unsaturated fatty acids, and
   c) hydrogenating said unsaturated fatty acids, optionally after converting said unsaturated fatty acids into their lower alkyl esters, to form unsaturated fatty alcohols having an iodine value of from about 85 to about 100.

11. A process as in claim 10 wherein said lauric oils are selected from palm kernel oil and coconut oil.

12. A process as in claim 10 including subjecting said lauric oils to pressure hydrolysis with water.

13. A process as in claim 10 wherein said functional crystallization step is carried out by rolling-up.

14. A process as in claim 10 including alkoxylating said unsaturated fatty alcohols.

15. A process as in claim 10 including alkoxylating, sulfating and neutralizing said unsaturated fatty alcohols.

16. A process as in claim 10 including sulfating and neutralizing said unsaturated fatty alcohols.

17. A process as in claim 10 including esterifying said unsaturated fatty alcohols with aliphatic carboxylic acids containing 1 to 22 carbon atoms and 0 or 1 to 3 double bonds.

18. A process as in claim 10 including mixing said unsaturated fatty alcohols with other saturated or unsaturated fatty alcohols containing 6 to 22 carbon atoms.

* * * * *